(12) United States Patent
Tamburin

(10) Patent No.: US 8,728,022 B2
(45) Date of Patent: May 20, 2014

(54) TAMPON APPLICATOR ASSEMBLY

(75) Inventor: Luca Tamburin, Hohentengen (DE)

(73) Assignee: Ruggli Projects AG (CH)

( * ) Notice: Subject to any disclaimer, the term of this patent is extended or adjusted under 35 U.S.C. 154(b) by 0 days.

(21) Appl. No.: 13/202,866

(22) PCT Filed: Feb. 23, 2010

(86) PCT No.: PCT/EP2010/001109
§ 371 (c)(1),
(2), (4) Date: Oct. 24, 2011

(87) PCT Pub. No.: WO2010/094507
PCT Pub. Date: Aug. 26, 2010

(65) Prior Publication Data
US 2012/0059306 A1    Mar. 8, 2012

(30) Foreign Application Priority Data

Feb. 23, 2009  (AT) ..................... 294/2009

(51) Int. Cl.
*A61F 13/30* (2006.01)
(52) U.S. Cl.
USPC ............ 604/14; 604/11; 604/317; 604/327; 604/328; 604/330
(58) Field of Classification Search
None
See application file for complete search history.

(56) References Cited

U.S. PATENT DOCUMENTS

| 3,696,812 | A | * | 10/1972 | Jaycox ............................ 604/18 |
| 4,276,881 | A | | 7/1981 | Lilaonitkul |
| 4,286,595 | A | | 9/1981 | Ring |
| 4,479,791 | A | * | 10/1984 | Sprague ......................... 604/14 |
| 4,650,459 | A | | 3/1987 | Sheldon |
| 4,676,773 | A | * | 6/1987 | Sheldon .......................... 604/16 |

(Continued)

FOREIGN PATENT DOCUMENTS

| DE | 69209085 T2 | 8/1996 |
| EP | 0221424 A1 | 5/1987 |

(Continued)

OTHER PUBLICATIONS

International Search Report, PCT/EP2010/001109, dated Mar. 31, 2010.

*Primary Examiner* — Tan-Uyen Ho
*Assistant Examiner* — Eric Bryant
(74) *Attorney, Agent, or Firm* — Lerner, David, Littenberg, Krumholz & Mentlik, LLP

(57) ABSTRACT

A tampon applicator assembly with an insertion end and a rear end containing a tampon made from absorbent material and an applicator comprising an outer tube and an inner tube able to slide in it in a telescopic arrangement, and the outer tube has at its insertion end at least two integrally formed, inwardly directed closure portions, and the tampon protrudes out from the insertion end of the inner tube by means of its insertion end and is completely accommodated inside the outer tube. The internal surface of the outer tube is smooth-walled from the closure portions to at least half the length of the outer tube without any inwardly extending projections. This assembly is extremely simple to manufacture. During use, the tampon is pushed forward by pushing the inner tube forward in the outer tube until it forces the closure portions of the outer tube outwards and protrudes out of the outer tube by an amount. When the inner tube is then pulled back, the tampon is held firmly in its pushed-forward position by the closure portions of the outer tube.

15 Claims, 2 Drawing Sheets

(56) References Cited

U.S. PATENT DOCUMENTS

| | | | |
|---|---|---|---|
| 4,891,042 A | 1/1990 | Melvin et al. | |
| 4,911,687 A * | 3/1990 | Stewart et al. | 604/15 |
| 5,330,421 A | 7/1994 | Tarr et al. | |
| 5,554,108 A | 9/1996 | Browning et al. | |
| 5,599,293 A | 2/1997 | Orenga et al. | |
| 5,800,377 A | 9/1998 | Campion et al. | |
| 5,823,988 A | 10/1998 | Orenga et al. | |
| 5,891,081 A * | 4/1999 | McNelis et al. | 604/14 |
| 6,416,488 B1 * | 7/2002 | Jackson et al. | 604/15 |
| 2002/0111578 A1 * | 8/2002 | Buzot | 604/14 |
| 2005/0197617 A1 | 9/2005 | Gorham et al. | |
| 2008/0195029 A1 | 8/2008 | Van Ingelem et al. | |

FOREIGN PATENT DOCUMENTS

| | | |
|---|---|---|
| EP | 0605016 A2 | 7/1994 |
| EP | 1704841 A1 | 9/2006 |
| WO | 9308779 A1 | 5/1993 |

* cited by examiner

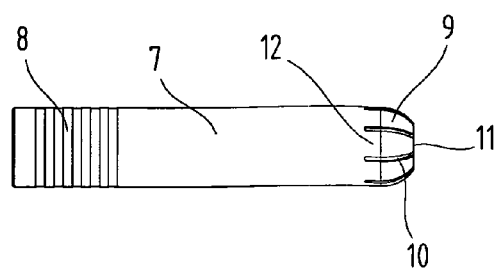
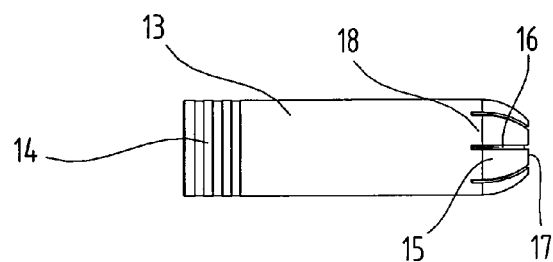
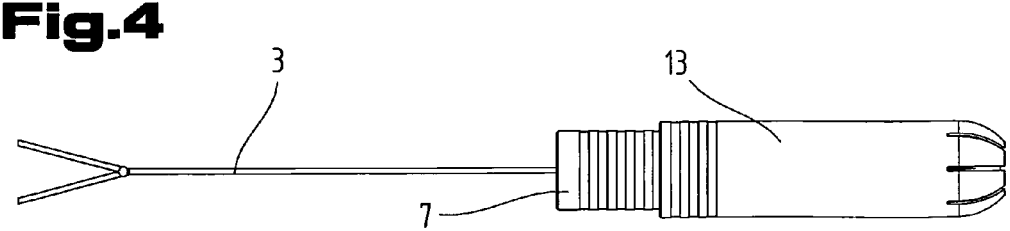
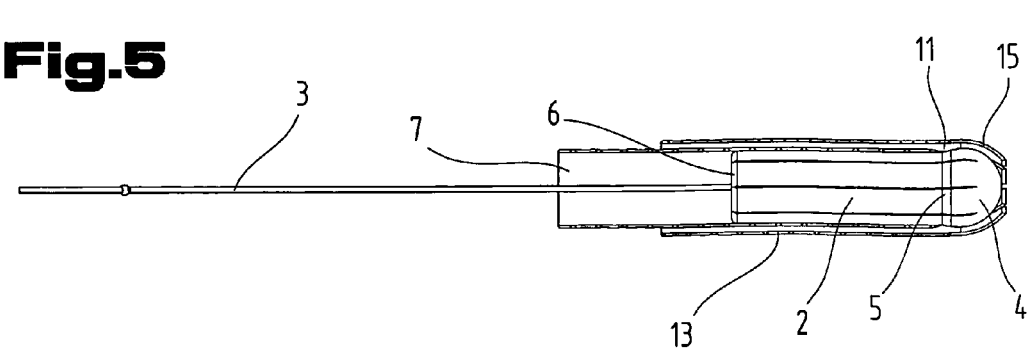

TAMPON APPLICATOR ASSEMBLY

CROSS REFERENCE TO RELATED APPLICATIONS

The present application is a national phase entry under 35 U.S.C. §371 of International Application No. PCT/EP2010/001109, filed Feb. 23, 2010, published in German, which claims the benefit of Austrian Patent Application No. A 294/2009, filed Feb. 23, 2009. The disclosures of said applications are incorporated by reference herein.

The invention relates to a tampon applicator assembly with an insertion end and a rear end containing a tampon of absorbent material and an applicator comprising an outer tube and an inner tube which is able to slide telescopically in it, and the outer tube has at least two integrally formed, inwardly directed closure portions at its insertion end, and the tampon protrudes out from the insertion end of the inner tube by means of its insertion end and is completely accommodated inside the outer tube.

Tampon applicators for introducing absorbent tampons into body orifices have long been known. In the case of one type of tampon applicator, the tampon is disposed inside a tube and ejector means are provided for ejecting the tampon from the tube. The ejector means might be another tube for example, which is able to slide telescopically in the first of the aforementioned tubes. One problem which occurs with these known tampon applicators is that if they are sold in a format ready for use, they are relatively long and therefore awkward to store and transport. As a means of solving this problem, co-called compact applicators were developed. These consist of two telescopic tubes and the tampon is disposed inside the inner tube and disposed together with it inside the outer tube in the state as sold. In order to use it, the inner tube must first of all be pulled back so that the tampon can be gripped during a subsequent backward movement and ejected from the outer tube. Retaining means of various types are used to ensure that the tampon is not moved back as the inner tube is pulled back but remains in the outer tube.

Patent EP1704841B1 discloses a compact applicator, where a tampon is accommodated in an inner tube in the packaged state, and it protrudes out from the inner tube in the insertion direction. The inner tube together with the tampon is accommodated in an outer tube, which is closed at the insertion end by means of a resilient closure portion of a spherical shape. Inwardly extending projections are disposed on the outer tube close to the base of the closure portions, which locate with the region of the tampon protruding out from the inner tube and prevent the tampon from being pulled out of the outer tube in the direction opposite the insertion direction when the inner tube is pulled back.

Producing retaining means of the type described above, for example, is associated with considerable costs. In the case of applicators made from plastic, such retaining means increase tooling costs considerably and in the case of applicators made from fiber, such as cardboard, it is practically impossible to produce retaining means in the form of inwardly extending projections whilst simultaneously providing closure portions on the end of the outer tube.

Against the background of this prior art, the objective of the invention is to propose a tampon applicator assembly which can be manufactured easily and inexpensively and the tampon is fully accommodated in the applicator prior to use and is therefore protected against any contact.

This objective is achieved by the invention due to the fact that the internal surface of the outer tube is smooth-walled from the closure portions to at least half the length of the outer tube without any inwardly extending projections.

The advantage of this solution proposed by the invention is that there is no need to provide inwardly extending projections as a means of holding the tampon back in the outer tube when the inner tube is pulled back. During use, the tampon is pushed forwards by pushing the inner tube forwards in the outer tube until it forces the closure portions of the outer tube outwards and protrudes out of the outer tube by a certain amount. When the inner tube is then pulled back, the tampon is held in its pushed-forward position in the outer tube by the closure portions of the outer tube.

Based on one embodiment of the invention, the closure portions of the outer tube are separated from one another by means of slots extending from the insertion end of the outer tube. Closure portions of this type are very simple to produce.

Based on another embodiment, an indentation is provided in the region of the ends of the slots remote from the insertion end extending in the circumferential direction of the outer tube between two slots. These indentations act as hinges for the respective adjacent closure portion when this closure portion is bent radially outwards by the tampon passing through it.

In a different embodiment, a gripping region is provided in the region of the end of the outer tube remote from the insertion end, comprising raised areas and/or recesses in the external surface of the outer tube. This prevents any sliding of the fingers when handling the assembly.

Based on another embodiment, the inner tube has at least two integrally formed, inwardly directed closure portions on its insertion end which are separated from one another by means of slots extending from the insertion end of the inner tube. These closure portions hold the tampon between them when the assembly is in the packaged state and snap inwards behind the tampon held in the outer tube once the inner tube has been pulled back so that they lie against the rear end of the tampon when the inner tube is subsequently pushed forwards.

Based on another embodiment, an indentation extending in the circumferential direction of the inner tube is provided on the inner tube respectively in the region of the ends of the slots remote from the insertion end. These indentations act as hinges for the respective adjacent closure portion when this closure portion is bent radially outwards by the tampon passing through it.

Based on another embodiment, a gripping region is provided in the region of the end of the inner tube remote from the insertion end, comprising raised areas or recesses in the external surface of the inner tube. The gripping region prevents any slipping of the fingers when the inner tube is moved axially in particular.

In the case of a preferred embodiment, the outer tube and/or the inner tube is made from a fiber-containing material, in particular cardboard. This material is inexpensive to manufacture and process and can be disposed of in an environmentally friendly manner.

Finally, in the case of another embodiment, the tampon has a head with a widened diameter at its insertion end. This offers a particularly practical way of preventing the tampon from being pushed through the closure portions of the outer tube into the outer tube once pushed forwards when the inner tube is pulled back.

The invention will be explained in more detail below with reference to examples of embodiments illustrated in the appended drawings.

Of these:

FIG. 1 illustrates a tampon for a tampon applicator assembly proposed by the invention;

FIG. 2 shows an inner tube for accommodating the tampon illustrated in FIG. 1;

FIG. 3 shows an outer tube for accommodating the inner tube illustrated in FIG. 2;

FIG. 4 is an external view of a tampon applicator assembly comprising the components illustrated in FIGS. 1 to 3 in the state as sold;

FIG. 5 is a view in section of the assembly illustrated in FIG. 4;

Figure 6:
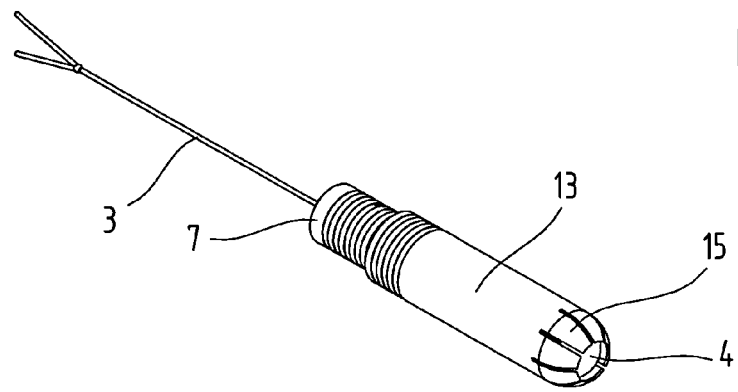
FIG. 6 is a perspective view of the assembly in the state as sold.

In the description given below, the end of all the components referred to as the insertion end is that intended to be inserted in a body orifice first when used. The insertion end is illustrated on the right-hand side of the drawings in all of FIGS. 1 to 9. Accordingly, the end of each component lying opposite the insertion end will be referred to as the rear end.

FIG. 1 illustrates an example of an embodiment of a tampon 1 for use in an assembly proposed by the invention. The tampon may be both a relatively weakly compressed tampon which cannot be inserted other than with the aid of an applicator or a so-called digital tampon which is compacted to the degree that it is stiff enough to be inserted by hand without the aid of an applicator. The tampon 1 comprises a tampon body 2 made from compressed, absorbent fiber material and has a withdrawal cord 3 to enable the tampon to be pulled out of the body cavity after use. In this example, the tampon body 2 has an approximately circular cylindrical part and, at the insertion end, on the right-hand side of the drawing, a rounded head 4, the external diameter of which is slightly bigger than the circular cylindrical part of the tampon body 2. Disposed between the circular cylindrical part and the head 4 is an annular abutment surface 5, the purpose of which will be explained later. The tampon body 2 has a rear end face 6 lying opposite the head 4. It should be stressed at this point that the assembly proposed by the invention is not restricted to the tampon described above and illustrated in FIG. 1.

FIG. 2 illustrates an example of an inner tube 7 for an assembly proposed by the invention. The inner tube 7 preferably has a gripping region 8 on its external surface close to the withdrawal end, the purpose of which is to prevent the fingers from slipping when the inner tube 7 is pushed axially in the outer tube 13 described below. The gripping region 8 comprises raised areas and/or recesses disposed in the external surface of the outer tube 13, which may be produced by punching for example. In the example illustrated, the gripping region 8 comprises circumferentially extending grooves and ribs disposed in alternation. At the insertion end, the inner tube 7 is at least partially closed off by a number of closure portions 9. The closure portions 9 are provided in the form of slots 10 in the material of the inner tube which are bent inwards so that their surfaces approximately assume the shape of a spherical portion. At least two slots 10 are provided and in the example illustrated, there are eight of them. The free ends of the closure portions 9 are preferably not quite pointed but have a terminal edge 11 extending at a right angle to the longitudinal axis of the inner tube 7. As a result, a circular opening is left free at the insertion end (see FIG. 6) and the insertion end therefore more or less has the shape of a spherical zone. To enable the closure portions 9 to be bent outwards more easily if necessary, a circumferentially extending indentation 12 may be provided in the inner tube 7 in their base region which acts as a hinge.

FIG. 3 illustrates an example of an outer tube 13 for an assembly proposed by the invention. The outer tube 13 is essentially of the same design as the inner tube 7 but is slightly shorter and has a larger diameter so that the outer tube 13 is able to accommodate the inner tube 7 in a telescopic arrangement. The outer tube 13 also has a gripping region 14 and closure portions 15 disposed at the insertion end, provided in the form of slots 16 in the material of the outer tube 13. At least two slots 16 are provided and in the example illustrated there are eight of them. The slots 16 extend from the insertion end of the outer tube and in the example illustrated run parallel with the longitudinal axis of the outer tube. However, they may also extend at an angle with respect to the longitudinal axis, in other words in the shape of a screw. The same also applies to the slots 10 in the inner tube 7. As is the case with the inner tube 7, the closure portions 15 of the outer tube 13 may have a terminal edge 17 and may be made easier to move by means of an indentation 18.

The inner tube 8 and outer tube 13 are preferably made from cardboard and are produced by winding a strip-shaped material in a screw pattern and gluing it.

FIGS. 4 and 5 illustrate the tampon assembly in the assembled state, FIG. 4 showing an external view and FIG. 5 a view in section. The components are assembled by firstly inserting the tampon 1 in the inner tube 7 from the rear end far enough for the head 4 of the tampon to force the closure portions 9 at the insertion end of the inner tube 7 outwards and protrude out of the inner tube at the insertion end. As may be seen from FIG. 5, the terminal edges 11 of the closure portions 9 lie on the external surface of the tampon body 2 due to their rebounding properties. The inner tube 7 with the tampon 1 accommodated in it is then inserted in the outer tube 13 from the rear end but at most only so far that the head 4 of the tampon lies against the internal surface of the closure portions 15. When the components are in this mutual position as illustrated in FIGS. 4 and 5, the assembly is packaged and dispatched for sale. One of the advantages of the invention is the fact that the tampon is completely enclosed by the applicator when the assembly is in the packaged state.

Figure 7:
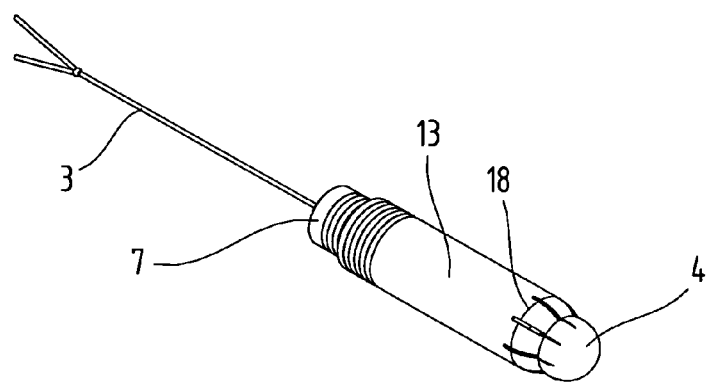
FIG. 7 is a perspective view of the assembly once the inner tube with the tampon has been pushed forwards.

FIGS. 6 to 9 illustrate the procedures involved when using the assembly proposed by the invention. FIG. 6 illustrates the assembly in the state as sold, based on the description given above with reference to FIGS. 4 and 5. As may be readily seen from FIG. 6, a circular opening is left free at the tip of the outer tube 13 if the closure portions 15 do not converge to a peak but have a terminal edge 17 instead. Before the inner tube 7 is pulled out of the outer tube 13 when the assembly is being used, the inner tube 7 must firstly be pushed forwards in the insertion direction far enough for the head 4 of the tampon 1 to protrude out from the outer tube 13, as illustrated in FIG. 7. This step may take place before or after inserting the device in a body orifice. The latter is preferable from a hygiene point of view and is also particularly recommendable if the tampon contains a material which should not come into contact with the body tissue until the tampon is more or less disposed in its intended position in the body.

From the position illustrated in FIG. 7, the inner tube 7 is then pulled back. As this happens, there is a tendency for the tampon 1 accommodated in the inner tube to be pulled backwards as well due to the friction which occurs between the external surface of the tampon and the internal surface of the outer tube 7. However, this is prevented by the closure portions 15 of the outer tube 13 which grip on the external surface of the tampon body 2 and on the abutment surface 5 and hold the tampon firmly in its position relative to the outer tube 13. The inner tube 7 is therefore moved backwards until its insertion end sits behind the rear end face 6 of the tampon body. At this instant, the closure portions 9 of the inner tube spring back inwards due to their elastic pre-tensioning. This effect is clearly perceptible because the resistance counteracting the act of pulling back the inner tube 7 caused by the friction between the inner tube and tampon suddenly disappears. This is the indication that the action of pulling back the inner tube should be terminated. In the position now assumed, illustrated in FIG. 8, it is still possible to insert the assembly in a body orifice, if this was not done before.

Figure 8:
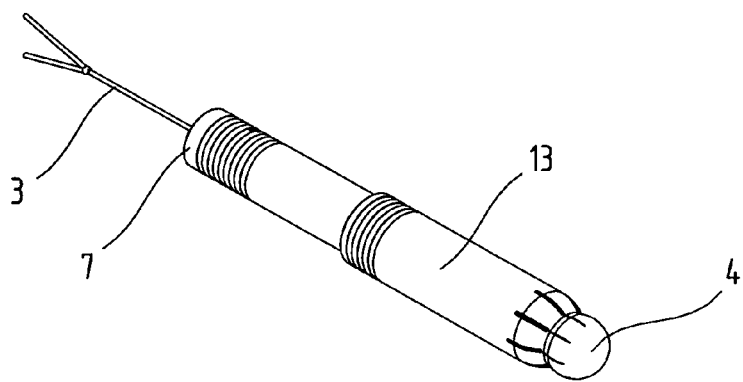
FIG. 8 is a perspective view of the assembly once the inner tube has been pulled back from the position illustrated in FIG. 7.
Figure 9:
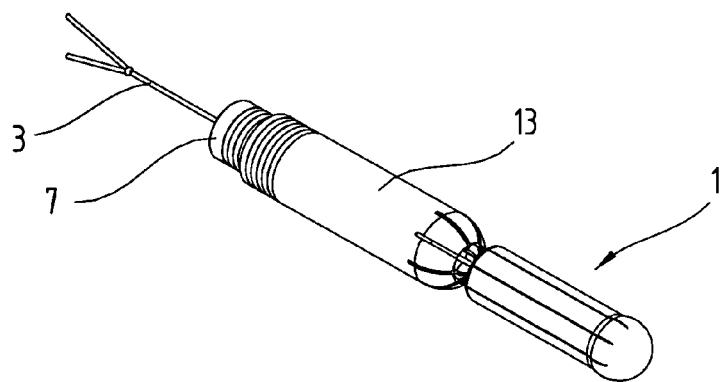
FIG. 9 is a perspective view of the components once the tampon has been completely ejected.

From the position illustrated in FIG. 8, the inner tube 7 is moved in the insertion direction so that the inwardly directed closure portions 9 of the inner tube 7 move into abutment with the rear end face 6 of the tampon body 2 and the tampon 1 is therefore ejected from the outer tube 13, as illustrated in FIG. 9.

The invention was described with reference to the example of an embodiment illustrated in the drawings but is not restricted to this example. Specifically, the tampon 1 need not necessarily have a head 4 with a bigger diameter. Instead, the ends of the closure portions 15 may act on the surface of the tampon in order to prevent the tampon from being pulled into the outer tube. The ends of the closure portions may be of a pointed design so that they penetrate the surface of the tampon when it is being pulled back. Alternatively or in addition, the tampon may be provided with recesses in its surface, which are conducive to the function of the ends of the closure portions. The recesses may be provided in the form of circumferentially extending grooves, for example.

For the sake of good order, finally, it should be pointed out that, in order to provide a clearer understanding of the design of the assembly, it and its components are illustrated to a certain extending out of scale and/or on an enlarged scale and/or on a reduced scale.

LIST OF REFERENCE NUMBERS

1 Tampon
2 Tampon body
3 Withdrawal cord
4 Head
5 Abutment surface
6 Rear end face
7 Inner tube
8 Gripping region
9 Closure portion
10 Slot
11 Terminal edge of 9
12 Indentation
13 Outer tube
14 Gripping region
15 Closure portion
16 Slot
17 Terminal edge of 15
18 Indentation

The invention claimed is:

1. A tampon applicator assembly with an insertion end and a rear end containing a tampon made from absorbent material and an applicator comprising an outer tube and an inner tube able to slide telescopically in the outer tube, and the outer tube has an insertion end including at least two integrally formed, inwardly directed closure portions which are separated from one another by slots extending from the insertion end of the outer tube, the inner tube has an insertion end including at least two integrally formed, inwardly directed closure portions having terminal edges which are separated from one another by slots extending from the insertion end of the inner tube, and a head of the tampon which protrudes out at the insertion end of the inner tube is held in place between the terminal edges of the at least two integrally formed, inwardly directed closure portions of the inner tube and is accommodated completely inside the outer tube when the tampon applicator assembly is in a packaged state, wherein the outer tube comprises a smooth, internal wall extending from the at least two integrally formed, inwardly directed closure portions toward the rear end of the tampon applicator assembly without any inwardly extending projections.

2. The tampon applicator assembly according to claim 1, comprising an indentation extending in a circumferential direction of the outer tube in a region of ends of the slots remote from the insertion end respectively between two slots.

3. The tampon applicator assembly according to claim 1, comprising a gripping region in a region of an end of the outer tube remote from the insertion end, comprising raised areas and/or indentations disposed on an external surface of the outer tube.

4. The tampon applicator assembly according to claim 1, comprising an indentation on the inner tube extending in a circumferential direction of the inner tube and arranged in a region of ends of the slots remote from the insertion end respectively between two slots.

5. The tampon applicator assembly according to claim 1, comprising a gripping region in a region of an end of the inner tube remote from the insertion end, comprising raised areas and/or recesses on an external surface of the inner tube.

6. The tampon applicator assembly according to claim 1, wherein the outer tube and/or the inner tube is made from cardboard.

7. The tampon applicator assembly according to claim 1, wherein the head of the tampon has a wider diameter at an insertion end of the tampon.

8. A tampon applicator assembly with an insertion end and a rear end containing a tampon made from absorbent material and an applicator comprising an outer tube and an inner tube able to slide telescopically in the outer tube, and the outer tube has an insertion end including at least two integrally formed, inwardly directed closure portions which are separated from one another by slots extending from the insertion end of the outer tube, the inner tube has an insertion end including at least two integrally formed, inwardly directed closure portions having terminal edges which are separated from one another by slots extending from the insertion end of the inner tube, and a head of the tampon which protrudes out at the insertion end of the inner tube is held in place between the terminal edges of the at least two integrally formed, inwardly directed closure portions of the inner tube and is accommodated completely inside the outer tube when the tampon applicator assembly is in a packaged state, wherein the outer tube comprises a smooth, internal wall extending from the at least two integrally formed, inwardly directed closure portions toward the rear end of the tampon applicator assembly without any inwardly extending projections; configured to insert the tampon in the inner tube from the rear end such that the head of the tampon forces the at least two integrally formed, inwardly directed closure portions at the insertion end of the inner tube outwards and such that the head of the tampon protrudes out of the inner tube at the insertion end; configured to insert the inner tube with the tampon accommodated in the inner tube into the rear end of the outer tube; and configured to push the inner tube forward in the outer tube such that the head of the tampon protrudes out from the insertion end of the outer tube.

9. The tampon applicator assembly of claim 8, further configured such that wherein when the inner tube is pulled back away from the insertion end of the outer tube, the at least two integrally formed, inwardly directed closure portions of the outer tube grip an external surface of the tampon and hold the tampon in a position relative to the outer tube.

10. The tampon applicator assembly of claim 9 wherein the external surface of the tampon comprises an abutment surface.

11. The tampon applicator assembly of claim 9, wherein when the inner tube is pulled back away from the insertion end of the outer tube, the at least two integrally formed, inwardly directed closure portions of the inner tube are arranged behind a rear end of the tampon in a position sprung back inwards for ejecting the tampon from the outer tube.

12. A method for positioning a tampon within a tampon applicator assembly, the tampon applicator assembly comprising an insertion end and a rear end containing a tampon made from absorbent material and an applicator comprising an outer tube and an inner tube able to slide telescopically in the outer tube, and the outer tube has an insertion end including at least two integrally formed, inwardly directed closure portions having terminal edges which are separated from one another by slots extending from the insertion end of the outer tube, the inner tube has an insertion end including at least two integrally formed, inwardly directed closure portions which are separated from one another by slots extending from the insertion end of the inner tube, and a head of the tampon which protrudes out at the insertion end of the insertion end of the inner tube is held in place between the terminal edges of the at least two integrally formed, inwardly directed closure portions of the inner tube and is accommodated completely inside the outer tube when the tampon applicator assembly is in a packaged state, wherein the outer tube comprises a smooth, internal wall extending from the at least two integrally formed, inwardly directed closure portions toward the rear end of the tampon applicator assembly without any inwardly extending projections, the steps comprising:

inserting the tampon in the inner tube from the rear end such that the head of the tampon forces the at least two integrally formed, inwardly directed closure portions at the insertion end of the inner tube outwards and such that the head of the tampon protrudes out of the inner tube at the insertion end;

inserting the inner tube with the tampon accommodated in the inner tube into the rear end of the outer tube;

pushing the inner tube forward in the outer tube such that the head of the tampon protrudes out from the insertion end of the outer tube;

pulling the inner tube back out away from the insertion end of the outer tube, thus ejecting the tampon from the inner tube.

13. The method of claim 12, wherein when the inner tube is pulled back away from the insertion end of the outer tube, the at least two integrally formed, inwardly directed closure portions of the outer tube grip an external surface of the tampon and hold the tampon in a position relative to the outer tube.

14. The method of claim 13 wherein the external surface of the tampon comprises an abutment surface.

15. The method of claim 13, wherein when the inner tube is pulled back away from the insertion end of the outer tube, the at least two integrally formed, inwardly directed closure portions of the inner tube are arranged behind a rear end of the tampon in a position sprung back inwards for ejecting the tampon from the outer tube.

* * * * *